United States Patent
Mundis et al.

(10) Patent No.: US 9,168,070 B2
(45) Date of Patent: Oct. 27, 2015

(54) GROWING SPINAL ROD SYSTEM

(71) Applicant: K2M, Inc., Leesburg, VA (US)

(72) Inventors: Gregory Mundis, San Diego, CA (US); Kevin R. Strauss, Columbia, MD (US); Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 68 days.

(21) Appl. No.: 14/021,162

(22) Filed: Sep. 9, 2013

(65) Prior Publication Data

US 2014/0074168 A1 Mar. 13, 2014

Related U.S. Application Data

(60) Provisional application No. 61/697,835, filed on Sep. 7, 2012.

(51) Int. Cl.
*A61B 17/70* (2006.01)

(52) U.S. Cl.
CPC ............ *A61B 17/705* (2013.01); *A61B 17/7014* (2013.01); *A61B 17/7025* (2013.01)

(58) Field of Classification Search
CPC ............. A61B 17/7025; A61B 17/705; A61B 17/7014
USPC .......................... 606/251, 252, 254–262, 278
See application file for complete search history.

(56) References Cited

U.S. PATENT DOCUMENTS

| | | | |
|---|---|---|---|
| 5,466,261 A | 11/1995 | Richelsoph | |
| 5,630,816 A * | 5/1997 | Kambin | 606/252 |
| 6,872,208 B1 * | 3/2005 | McBride et al. | 606/86 A |
| 7,842,071 B2 * | 11/2010 | Hawkes | 606/252 |
| 7,927,357 B2 | 4/2011 | Sacher et al. | |
| 7,942,908 B2 | 5/2011 | Sacher et al. | |
| 7,955,357 B2 | 6/2011 | Kiester | |
| 8,162,984 B2 | 4/2012 | Weirich et al. | |
| 8,475,499 B2 | 7/2013 | Cournoyer et al. | |
| 8,568,457 B2 | 10/2013 | Hunziker | |
| 8,585,740 B1 | 11/2013 | Ross et al. | |
| 2006/0195088 A1 | 8/2006 | Sacher et al. | |
| 2008/0027436 A1 | 1/2008 | Cournoyer et al. | |
| 2008/0300630 A1 * | 12/2008 | Bonnema et al. | 606/246 |
| 2009/0036924 A1 * | 2/2009 | Egli et al. | 606/246 |

(Continued)

FOREIGN PATENT DOCUMENTS

WO    WO 2008/021107    2/2008

OTHER PUBLICATIONS

European Search Report dated Jan. 16, 2014 in European Application No. EP 13 18 3506.

*Primary Examiner* — Jan Christopher Merene
*Assistant Examiner* — Atiya Mahmud
(74) *Attorney, Agent, or Firm* — Carter, DeLuca, Farrell & Schmidt, LLP

(57) ABSTRACT

A growing spinal rod system is configured to grow in response to the growth of a patient. The growing spinal rod system includes a housing, a spacer, and a sliding spinal rod. The housing includes a stepped passage therethrough. The spacer is disposed within the stepped passage and defines a through hole. The spacer includes a plurality of ribs biased inwards and into the through hole. The sliding spinal rod is slidably inserted through the through hole of the spacer. The sliding spinal rod moves the plurality of ribs outwards. The plurality of ribs permits the sliding spinal rod to extend from the housing and inhibit the sliding spinal rod from retracting into the housing.

14 Claims, 8 Drawing Sheets

(56) References Cited

U.S. PATENT DOCUMENTS

| | | |
|---|---|---|
| 2010/0094345 A1* | 4/2010 | Saidha et al. .................. 606/250 |
| 2010/0106192 A1 | 4/2010 | Barry |
| 2011/0184463 A1 | 7/2011 | Schwend |
| 2012/0130428 A1 | 5/2012 | Hunziker |
| 2012/0271353 A1 | 10/2012 | Barry |
| 2013/0096615 A1 | 4/2013 | Kiester |
| 2013/0172934 A1* | 7/2013 | Walker et al. .................. 606/252 |
| 2013/0282064 A1 | 10/2013 | Arnin |

* cited by examiner

GROWING SPINAL ROD SYSTEM

CROSS-REFERENCE TO RELATED APPLICATIONS

This application claims priority to, and the benefit of, U.S. Provisional Application Ser. No. 61/697,835 filed Sep. 7, 2012, the disclosure of which is hereby incorporated by reference in its entirety.

BACKGROUND

1. Technical Field

The present disclosure relates to a device for use in orthopedic surgeries and, more specifically, to a growing spinal rod system.

2. Discussion of Related Art

The human spine is comprised of thirty-three vertebrae at birth and twenty-four as a mature adult. The vertebra includes the vertebral body and posterior elements, including the spinous process, transverse processes, facet joints, laminae, and pedicles. The vertebral body consists of a cortical shell surrounding a cancellous center. Between each pair of vertebrae is an intervertebral disc, which maintains the space between adjacent vertebrae and acts as a cushion under compressive, bending, and rotational loads and motions. A healthy intervertebral disc consists mostly of water in the nucleus pulposus, which is the center portion of the disc. The water content gives the nucleus a spongy quality and allows it to absorb spinal stresses.

Scoliosis is a medical condition whereby the spine is curved from side to side or front to back and may be rotated about its longitudinal axis. Typical treatment involves observation in order to determine the rate of progression and external bracing to help ensure any future growth of the spine follows the desired path and orientation.

Surgical intervention is warranted when the likelihood of curve or rotation progression is high or if a significant amount of pain or other general health risks are experienced. In these instances, a spinal fusion of various segments may be performed in order to stabilize the scoliotic curve. In younger patients, performing a spinal fusion is less desirable since it will interfere with the normal growth of the individual.

In an effort to maintain normal growth or height, while correcting a younger patient's abnormally curved spine, devices known as "growing spinal rods" have been developed. Growing spinal rods provide structure, stability, and correction to the spine, but also allow the spinal rod to lengthen without the need for replacing or adding devices to the original construct.

Growing spinal rod systems on the market today require a surgical procedure for manually increasing the length of the spinal rod; e.g., by loosening one or more set screws, providing distraction between two spinal rod segments, and then re-tightening. Systems such as this require a surgical procedure approximately every six months for several years.

Accordingly, a continuing need exists for a device that allows for skeletal growth and more specifically, spine growth, without repeated surgical intervention while maintaining the desired spinal correction.

SUMMARY

In aspects of the present disclosure, a growing spinal rod system includes a housing, one or more spacers, and a first spinal rod. The housing defines a longitudinal axis and a stepped passage. The stepped passage is disposed about the longitudinal axis and includes a first and second end. A diameter of the first end is less than a diameter of the second end. The spacers are disposed within the stepped passage of the housing about the longitudinal axis thereof. Each spacer includes a ring defining a through hole coaxial with the longitudinal axis and a plurality of ribs extending from the ring towards the first end of the stepped passage. The plurality of ribs are biased inwards. The first spinal rod is slidably inserted through the through holes of the spacers and extends from the housing through the first end of the stepped passage. The first spinal rod urges the plurality of ribs outwards when the first spinal rod is inserted through the through hole of the at least one spacer. The ribs permit the first spinal rod to extend from the housing through the first end of the stepped passage and inhibit the first spinal rod from retracting into the housing through the first end of the stepped passage.

In aspects of the present disclosure, each spacer includes a plurality of mating protrusions extending from the ring toward the second end of the stepped passage. The plurality of ribs may define mating slots between adjacent ribs. Each mating slot may be sized and configured to receive a respective mating protrusion. In embodiments, the growing spinal rod system includes a first spacer and a second spacer and each of the mating protrusions of the first spacer are received by a respective mating slot of the second spacer.

In aspects of the present disclosure, the growing spinal rod system includes a second spinal rod including a first end insertable into the second end of the stepped passage. The first end of the second spinal rod defines mating recesses. Each of the mating recesses receives a respective mating protrusion of a spacer. The first end of the second spinal rod engages the ring of the spacer when the mating protrusions are received within the mating recesses.

In aspects of the present disclosure, the first end of the stepped passage includes a flat first keyed surface and the first spinal rod includes a longitudinal groove. The groove mates with the first keyed surface of the first end to rotatably fix the first spinal rod relative to the housing. In embodiments, the first spinal rod includes a first portion having a first diameter and a second portion having a second diameter larger than the first diameter of the first portion. The groove is formed in the second portion. In some embodiments, the groove extends substantially along a length of the second portion and the second portion includes a lip adjacent an end of the second portion. The lip extends above the groove and is configured to stop the end of the second portion from extending through the first end of the stepped passage. In particular embodiments, the housing defines a blind hole orthogonal to the longitudinal axis adjacent the first end of the stepped passage. The blind hole penetrates the stepped passage. In certain embodiments, the housing includes a set screw that is insertable through the blind hole to limit the travel of the first spinal rod relative to the housing.

In aspects of the present disclosure, the housing defines a blind hole orthogonal to the longitudinal axis adjacent the second end of the stepped passage. The blind hole penetrates the stepped passage. In embodiments, the housing includes a set screw insertable within the blind hole to longitudinally fix the second spinal rod relative to the housing. In some embodiments, the second end of the stepped passage includes a flat second keyed surface and the second spinal rod includes a flat top surface that mates with the second keyed surface to rotatably fix the second spinal rod relative to the housing. In aspects of the present disclosure, the housing includes a cutout that is configured to permit visualization of the stepped passage.

In aspects of the present disclosure, a method of spinal surgery includes inserting a growing spinal rod system into a spinal construct, adjusting the length of the growing spinal rod system to a desired length, and securing a portion of a first spinal rod and a portion of a second spinal rod to respective pedicle screws of the spinal construct. Adjusting the length of the growing spinal rod system may include loosening a set screw adjacent a first end of a stepped passage to free the first spinal rod and extending the first spinal rod from the housing through the first end. The housing may include a cutout and adjusting the length of the growing spinal rod system may include visualizing the length of the first spinal rod through the cutout. In embodiments, visualizing the length of the first spinal rod through the cutout includes visualizing the length of the second spinal rod using fluoroscopy.

The method may include permitting the first spinal rod to extend from the housing through the first end of the stepped passage in response to growth of a patient.

In aspects of the present disclosure, a method of assembling a growing spinal rod system includes sliding a first spinal rod substantially through a plurality of spacers, loading the plurality of spacers and the first spinal rod into the housing through a second end of the housing by engaging a ring of one of the plurality of spacers with an end of a second spinal rod until a first end of one of the plurality of spacers abuts an end of a stepped passage that is proximal to a first end of the housing, and fixing the second spinal rod relative to the housing. The method may include limiting the travel of the first spinal rod relative to the housing after loading the plurality of spacers and the first spinal rod into the housing.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
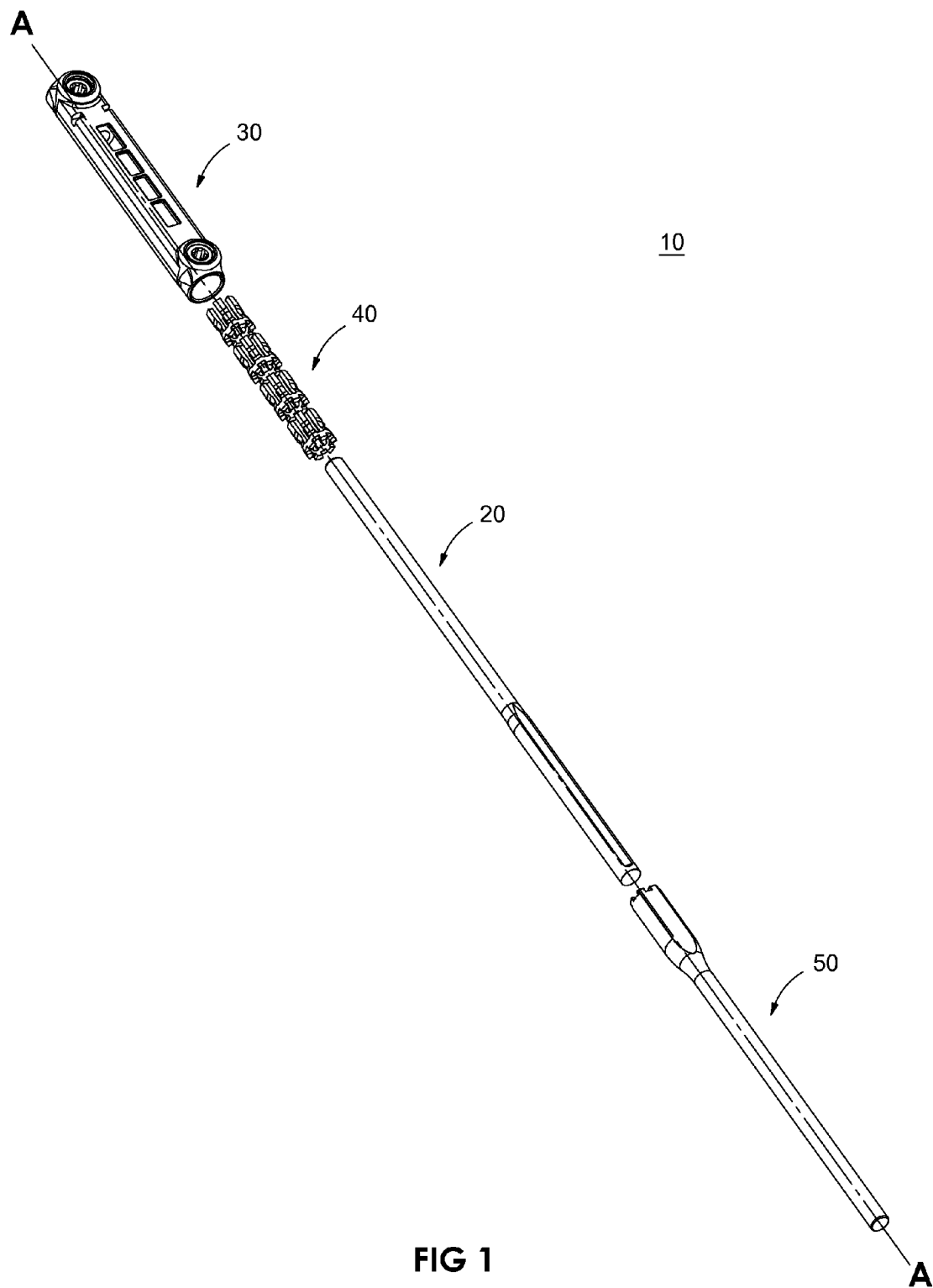
FIG. 1 is a perspective view of a growing spinal rod system in accordance with the present disclosure, with parts separated.
Figure 2A:
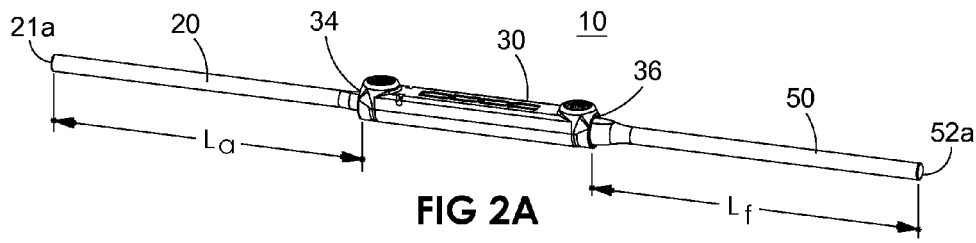
FIGS. 2A-E are a progression of perspective views of the growing spinal rod system of FIG. 1 showing the sliding spinal rod adjusted to extend various lengths from the housing.
Figure 2B:
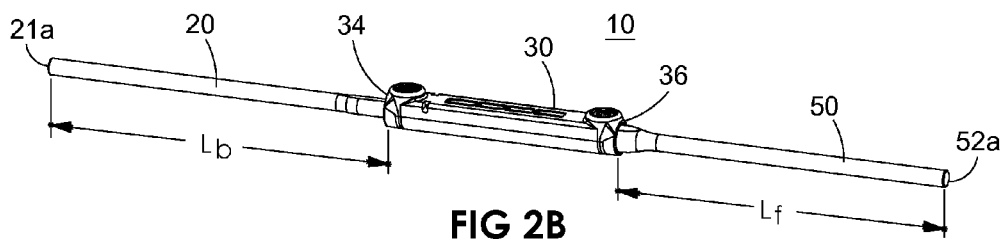
Figure 2C:
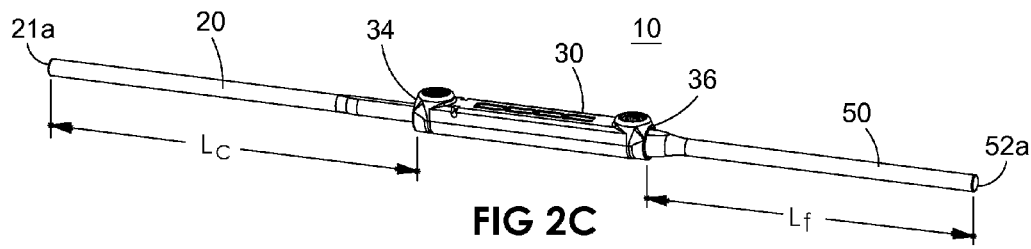
Figure 2D:
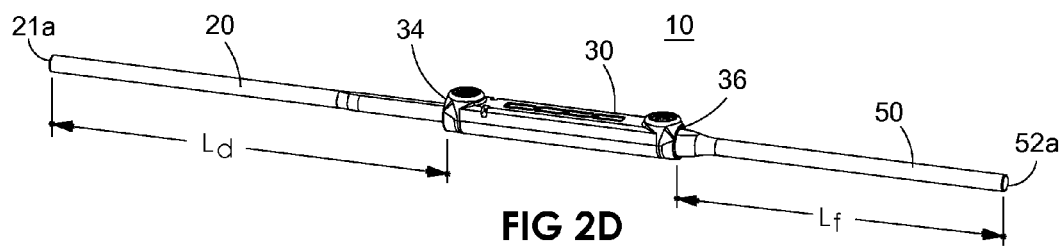
Figure 2E:
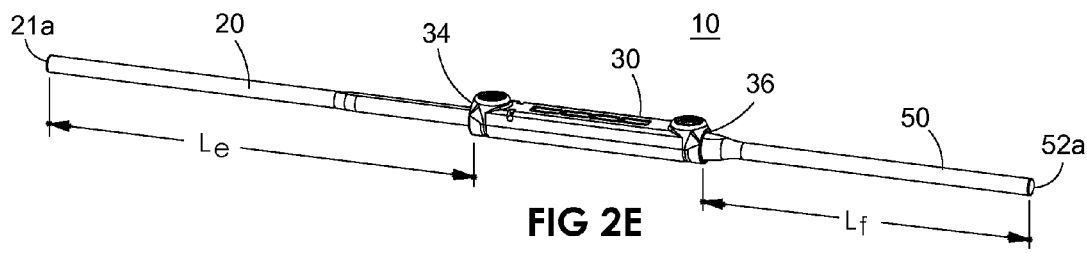

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

With reference to FIG. 1, a growing spinal rod system or rod system 10 is provided in accordance with the present disclosure includes a housing 30, a plurality of spacers 40, a first or sliding spinal rod 20, and a second or fixed spinal rod 50. The housing 30 defines a longitudinal axis A-A. The plurality of spacers 40, the sliding spinal rod 20, and the fixed spinal rod 50 are disposed about the longitudinal axis A-A as detailed below.

Referring to FIGS. 2A-E, when the rod system 10 is assembled, as detailed below, the spacers 40 (FIG. 1) and the fixed spinal rod 50 are fixed relative to the housing 30 defining a fixed length $L_f$ from a second end 36 of the housing 30 to a second end 52a of the fixed spinal rod and the sliding spinal rod 20 is configured to extend from the housing 30 defining a plurality of adjustable lengths $L_a$, $L_b$, $L_c$, $L_d$, and $L_e$ between a first end 21a of sliding spinal rod 20 and a first end 34 of the housing 30. As such, the overall length of the growing spinal rod system 10 is the sum of $L_f$ plus a length of the housing 30 plus the length of the sliding spinal rod 20 (e.g., $L_a$-$L_e$). The minimum length of the growing spinal rod system 10 is $L_f$ and the length of the housing plus $L_a$ and the maximum length of the growing spinal rod system 10 is $L_f$ plus the length of the housing plus $L_e$. The growing spinal rod system 10 is adjustable to any length between the minimum length and the maximum length.

Figure 3:
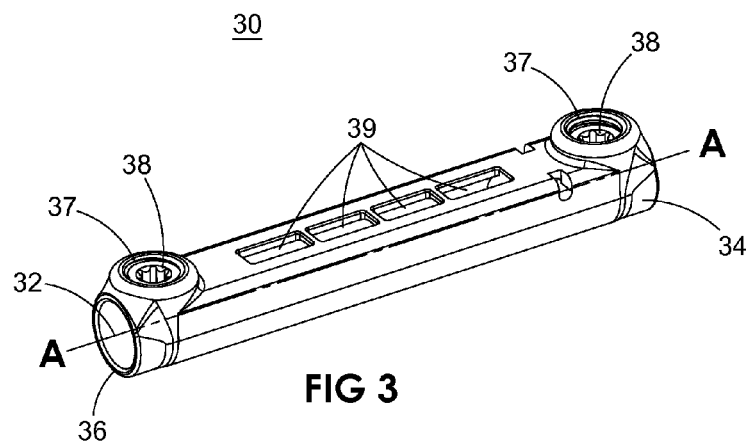
FIG. 3 is a perspective view of the housing of the growing spinal rod system of FIG. 1.
Figure 4:
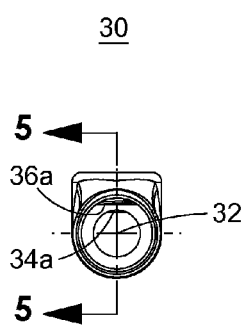
FIG. 4 is an end view of the housing of FIG. 3 from the large diameter end thereof.
Figure 5:
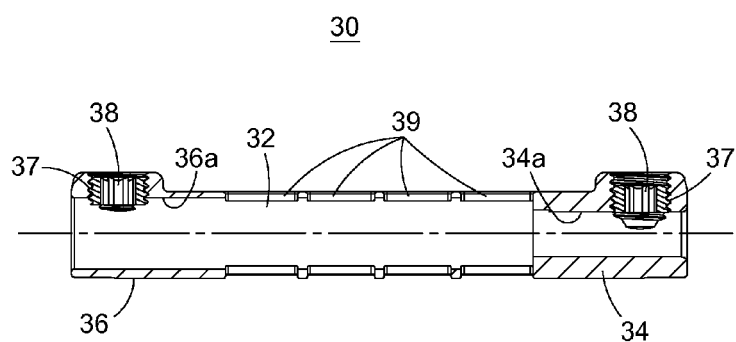
FIG. 5 is a side longitudinal cross-sectional view taken along the line 5-5 of FIG. 4.

Referring to FIGS. 3-5, the housing 30 defines a stepped passage 32 about the longitudinal axis A-A and defines two blind holes 37 orthogonal to the longitudinal axis A-A. The stepped passage 32 has a first or small diameter end 34 and a second or large diameter end 36. The small diameter end 34 includes a flat first keyed surface 34a and the large diameter end 36 includes a flat second keyed surface 36a. One of the blind holes 37 is positioned adjacent to the small diameter end 34 penetrating the first keyed surface 34a and the other of the blind holes 37 is positioned adjacent to the large diameter end 36 penetrating the second keyed surface 36a. In embodiments, the housing 30 defines a single blind hole 37 positioned adjacent the large diameter end 36. The blind holes 37 penetrate into the stepped passage 32 and are threaded to receive set screws 38. Set screws 38 are threaded to cooperate with the threads of the blind holes 37. In embodiments, second keyed surface 36a is disposed on set screws 38. The housing 30 may define cutouts 39 in a top surface thereof that permit visualization of the stepped passage 32. In embodiments, the cutouts 39 may extend through the bottom surface of the housing 30. The cutouts 39 may be evenly spaced to provide visualization of the length of the sliding spinal rod 20 (FIG. 1) disposed within stepped passage 32 as detailed below. In some embodiments, cutouts 39 provide visualization of the rod location using an imaging modality, e.g., fluoroscopy.

Figure 6:
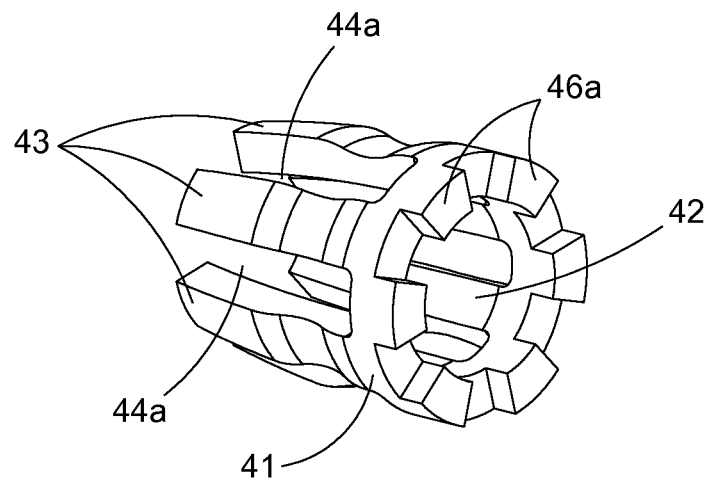
FIG. 6 is a perspective view of a spacer of the growing spinal rod system of FIG. 1.
Figure 7:
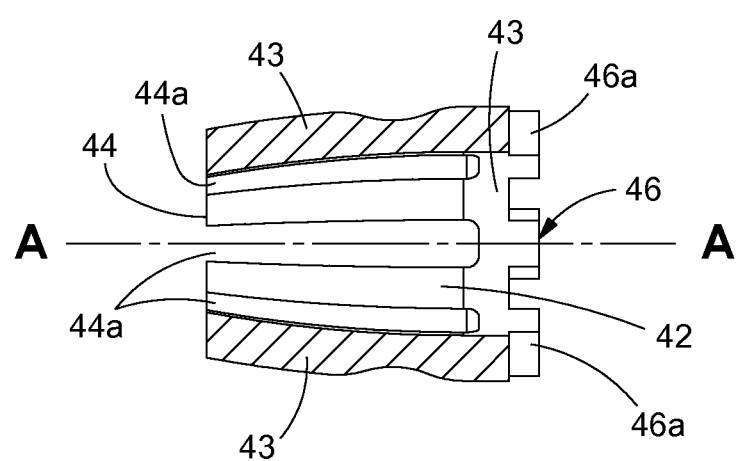
FIG. 7 is a side longitudinal cross-sectional view of the spacer of FIG. 6 taken along the longitudinal axis thereof.

Referring to FIGS. 6 and 7, each spacer 40 includes a ring 41 and ribs 43. The ribs 43 extend from the ring 41 towards a first end 44 of the spacer 40. The ring 41 defines a through hole 42 sized and configured to slidably receive the sliding spinal rod 20 (FIG. 1). The ribs 43 may be biased inward to at least partially interfere with the through hole 42. As shown, each spacer 40 has a length of about 10 mm along the longitudinal axis A-A; however, it is contemplated that each spacer 40 can be made in various lengths in a range of about 5 mm to about 50 mm. As shown, each spacer 40 has the same length; however, it is contemplated that at least one of the spacers 40 may have a length different from another of the spacers 40. The ribs 43 of each spacer 40 may allow for flexing of the spacer between the ring 41 and the first end 44. The ribs 43 define mating slots 44a therebetween. Mating protrusions 46a extend towards a second end 46 of each spacer 40 from the ring 41. The spacers 40 are sized and configured to be disposed within the stepped passage 32 of housing 30. The spacers 40 are aligned such that the first end 44 of each spacer 40 faces the small diameter end 34 of the housing 30 and the second end 46 of each spacer 40 faces the large diameter end 36 of the housing 30. Each mating protrusion 46a of each spacer is received within a respective mating slot 44a of an adjacent spacer 40.

Figure 8:
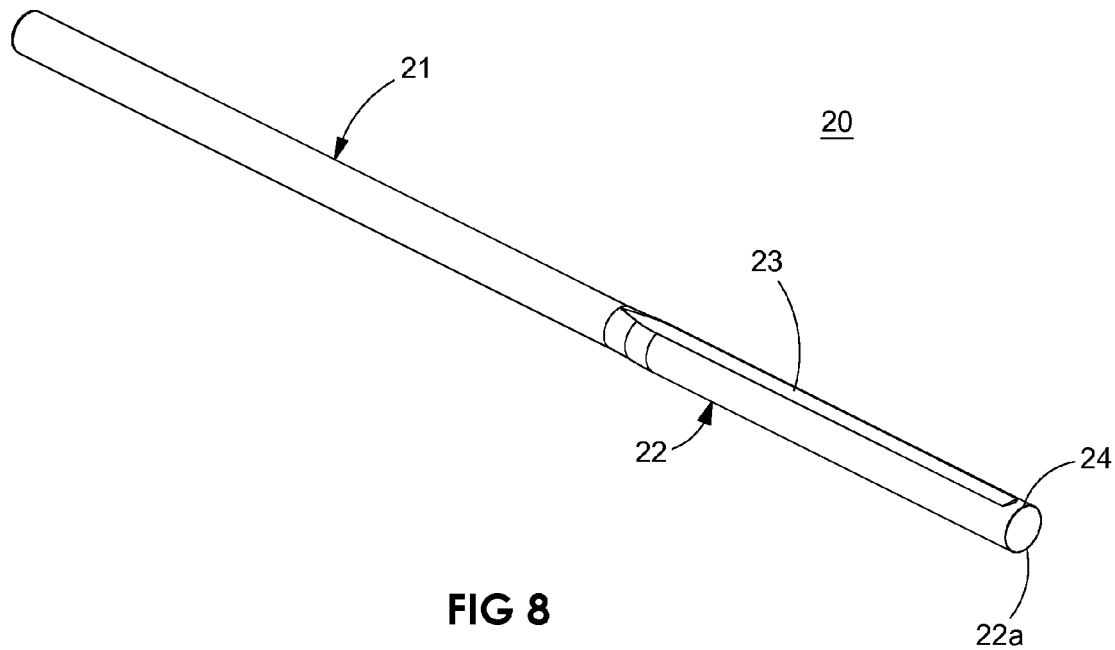
FIG. 8 is a perspective view of the sliding spinal rod of the growing spinal rod system of FIG. 1.

Referring to FIG. 8, sliding spinal rod 20 has a first portion 21 defining a first diameter and a second portion 22 defining a second diameter. As shown, the second diameter of the second portion 22 is larger than the first diameter of the first portion 21; however, it is contemplated that the first and second diameter of the first and second portions 21, 22, respectively, may be the same. The first and second portions 21, 22 of sliding spinal rod 20 are sized and configured to slide through the through hole 42 (FIG. 7) of the spacers 40 and substantially through the small diameter end 34 (FIG. 5) of the stepped passage 32 of housing 30. The second portion 22 includes a groove 23 substantially along the length thereof and a lip 24 adjacent an end 22a of the second portion 22. The groove 23 is configured to mate with the first keyed surface 34a (FIG. 7) of the small diameter end 34 of the housing 30 to radially fix the sliding spinal rod 20 relative to the housing 30. The lip 24 extends above groove 23 to engage the first keyed surface 34a to retain sliding spinal rod 20 within housing 20 as detailed below. The groove 23 may be cut from the second diameter of the second portion 22 and the lip 24 may have a diameter equal to the second diameter of the second portion 22. Groove 23 may also provide a flat surface for the set screws 38 (FIG. 5) to engage the sliding spinal rod 20 to lock or longitudinally fix or limit the travel of the sliding spinal rod 20 relative to the housing 30.

Figure 9:
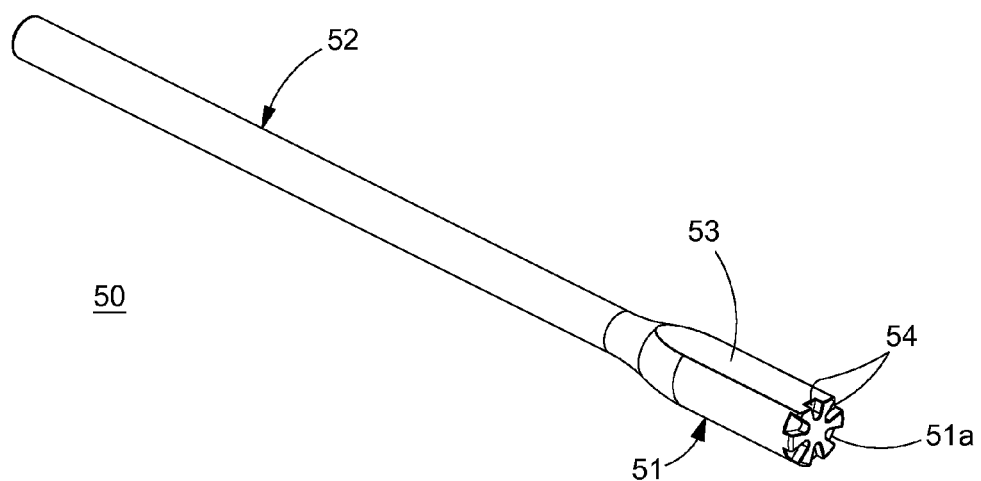
FIG. 9 is a perspective view of the fixed spinal rod of the growing spinal rod system of FIG. 1.
Figure 12:
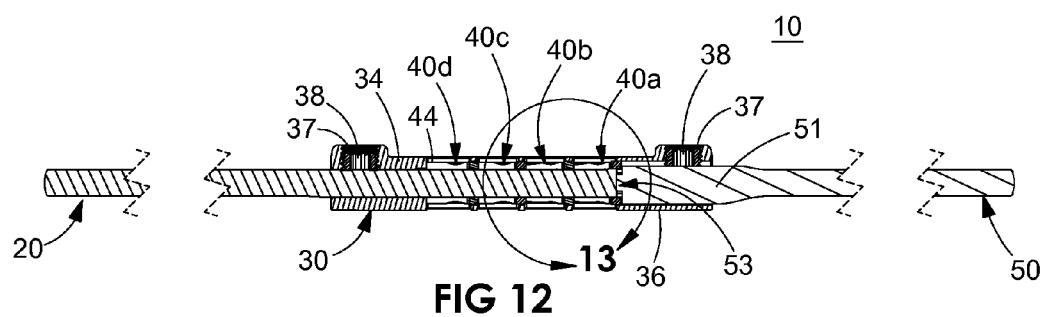
FIG. 12 is a side cross-sectional view taken along the line 12-12 of FIG. 11.
Figure 13:
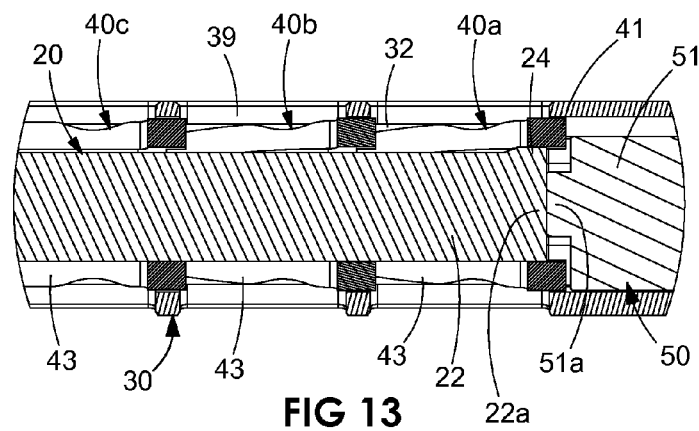
FIG. 13 is an enlargement of the detail area 13 shown in FIG. 12.
Figure 14:
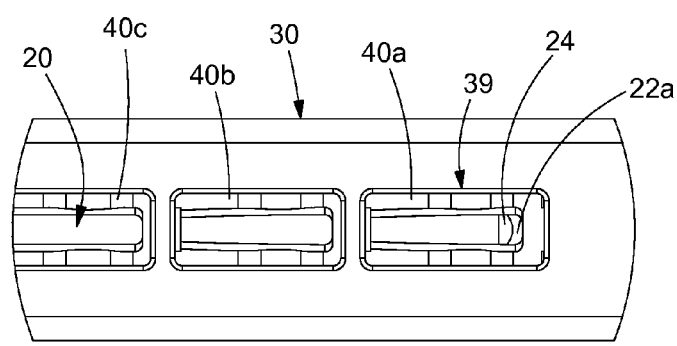
FIG. 14 is an enlargement of the detail area 14 shown in FIG. 11.
Figure 15:
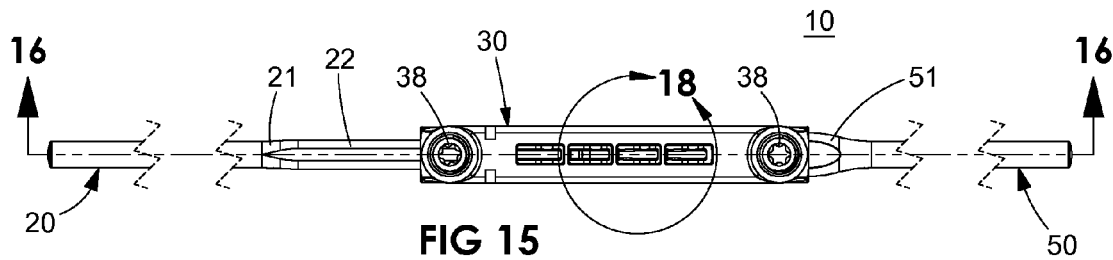
FIG. 15 is a top view of the growing spinal rod system of FIG. 11 with the end of the second portion of the sliding spinal rod positioned within the through hole of the third spacer.
Figure 16:
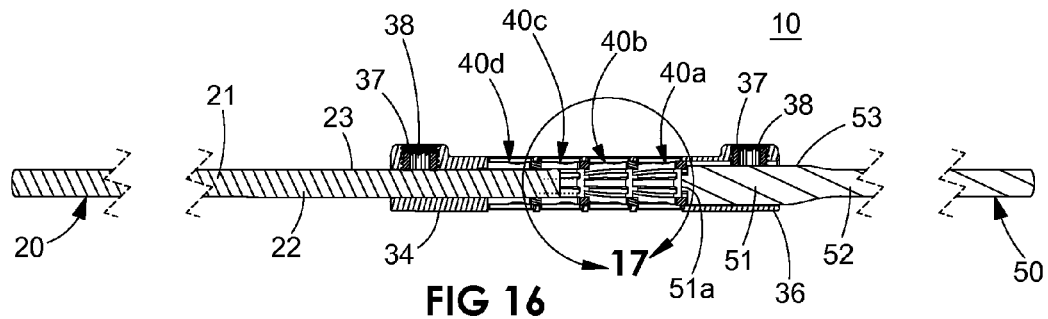
FIG. 16 is a side cross-sectional view taken along the line 16-16 of FIG. 15.
Figure 17:
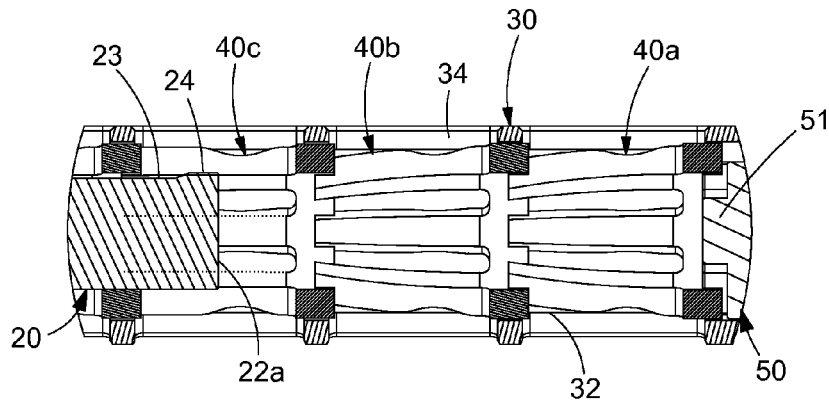
FIG. 17 is an enlargement of the detail area 17 shown in FIG. 16.

Referring to FIG. 9, the fixed spinal rod 50 includes a first section 51 and a second section 52. The first section 51 defines a first diameter and the second section 52 defines a second diameter. As shown, the first diameter of the first section 51 is greater than the second diameter of the second section 52; however, it is also contemplated that the first and second diameters of the first and second sections 51, 52, respectively, may be the same. The first diameter of the first section 51 is larger than the diameter of the through hole 42 (FIG. 7) of the ring 41 of the spacers 40 such that an end 51a of the first section 51 engages ring 41 of a spacer 40. In embodiments, the second diameter of the second section 52 of the fixed spinal rod 50 is the same as the first diameter of the first portion 21 of the sliding spinal rod 20, e.g., the first portion 21 and the second section 52 may have a diameter in the range of about 5 mm to about 7 mm. The end 51a of the first section 51 may define mating recesses 54. Each mating recess 54 is configured to receive a respective mating protrusion 46a of a spacer 40. The first section 51 includes a flat top surface 53 configured to mate with the second keyed surface 36a of the housing 30 to rotatably fix the fixed spinal rod 50 relative to the housing 30. The first section 51 is slidably received through the large diameter end 36 of the housing 30 as shown in FIG. 12.

Referring to FIGS. 10-13, the assembly of growing spinal rod system 10 is described in accordance with the present disclosure. During assembly, the set screws 38 are backed out such that the set screws 38 do not interfere with the stepped passage 32 of the housing 30.

Figure 10:
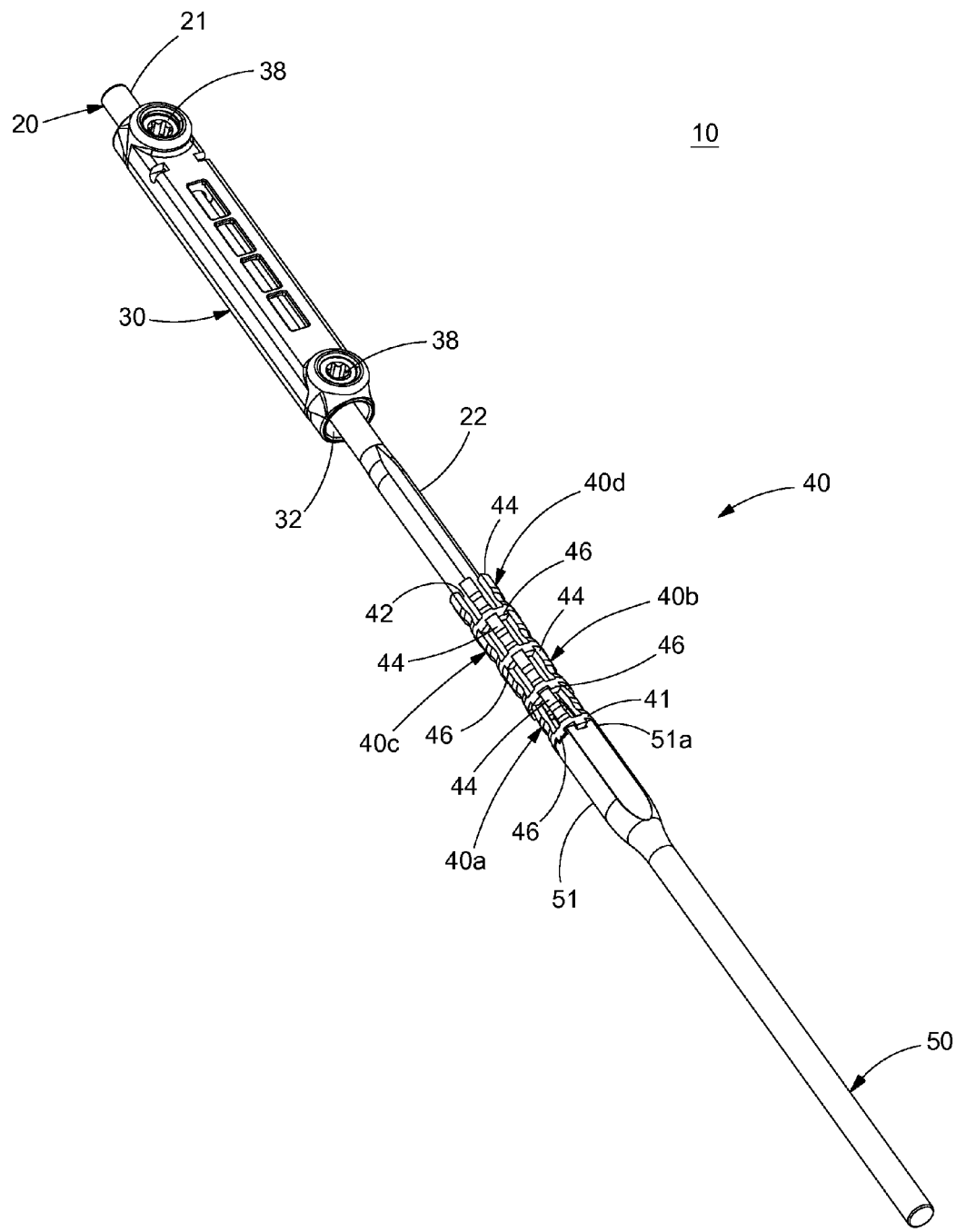
FIG. 10 is a perspective view of the growing spinal rod system of FIG. 1 with the sliding spinal rod slidably received by the housing and the plurality of spacers.
Figure 11:
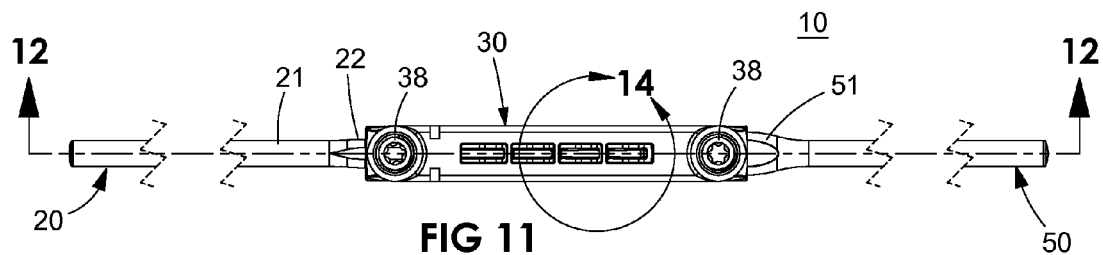
FIG. 11 is a top view of the growing spinal rod system of FIG. 1 with the plurality of spacers loaded within the housing and the sliding spinal rod slidably received within the housing.

With particular reference to FIG. 10, the first portion 21 of the sliding spinal rod 20 is slid through the through hole 42 of each of the spacers 40 such that the first portion 21 passes through the second end 46 before the first end 44 of each of the spacers 40. The ribs 43 of each spacer 40 are displaced outward around second portion 22 as the first portion 21 of sliding spinal rod 20 passes through the through hole 42. The engagement of the ribs 43 of spacers 40 permit translation of spinal rod 20 through each spacer 40 from the second end 46 to the first end 44 thereof and inhibit translation of spinal rod 20 from the first end 44 to the second end 46 thereof. As shown, rod system 10 includes four spacers 40a-d; however, it is contemplated that rod system 10 may include a fewer or a greater number of the spacers 40. The spacers 40 are slid over the first portion 21 of the sliding spinal rod 20 and over the second portion 22 of the sliding spinal rod 20 until the ring 41 of a first spacer 40a is at or adjacent to the lip 24 (FIG. 13) of sliding spinal rod 20.

The first end 51a of fixed spinal rod 50 engages the ring 41 of the first spacer 40a to insert or slide the sliding spinal rod 20 and the spacers 40 into the housing 30. As the sliding spinal rod 20 is inserted into the housing 30, the first portion 21 extends from the small diameter end 34 of the stepped passage 32. The spacers 40 slide through the stepped hole 32 of housing 30 until the first end 44 of a fourth spacer 40d, i.e., the last of the spacers 40 slid over sliding spinal rod 20, engages the small diameter end 34 of the housing 30 as shown in FIG. 12. When the fourth spacer 40d engages the small diameter end 34 of the housing 30, each mating protrusion 46a of each spacer 40 is received within a respective mating slot 44a of the adjacent spacer 40 to load the spacers 40 into housing 30, i.e., the mating protrusions 46a of fourth spacer 40d are received within a respective mating slots 44a of a third spacer 40c, the mating protrusions 46a of the third spacer 40c are received within a respective mating slots 44a of a second spacer 40b, and the mating protrusions 46a of the second spacer 40b are received within a respective mating slots 44a of the first spacer 40a. In embodiments, the housing 30 includes features to inhibit the spacers 40 from backing out of the stepped passage 32 after the spacers 40 are loaded therein. The end 22a of the second portion 22 of the sliding spinal rod 20 may be adjacent to or engaged with the end 51a of the first section 51 of the fixed spinal rod 50 as shown in FIG. 12.

When the spacers 40 are loaded into the housing 30, the first end 51a of the fixed spinal rod 50 is engaged with the ring 41 of the first spacer 40a and is positioned past the blind hole 37 of the housing 30 adjacent the large diameter end 36 of the stepped passage 32. The set screw 38 adjacent the large diameter end 36 of the housing 30 is tightened to engage and longitudinally fix the fixed spinal rod 50 relative to the housing 30. The set screw 38 may engage the flat top surface 53 of the fixed spinal rod 50 to longitudinally fix the fixed spinal rod 50 relative to the housing 30. In embodiments, the set screw 38 adjacent the small diameter end 34 of the housing 30 is tightened to engage and limit the travel of the sliding spinal rod 20 relative to the housing 30. Limiting the travel of the sliding spinal rod 20 may assist in the insertion of the rod system 10 into a spinal construct (not shown).

Referring to FIGS. 11-18, the use of the rod system 10 is described in accordance with the present disclosure. The rod system 10 is inserted into the surgical site (not shown) with the fixed spinal rod 50 longitudinally fixed or locked in place by a set screw 38 as described above. The sliding spinal rod 20 may also be longitudinally fixed or locked in place by a set screw 38 or be free to extend from the housing 30 through the small diameter end 34 of the stepped passage 32. It will be appreciated that the engagement of the ribs 43 of the spacers 40 with the sliding spinal rod 20 inhibits retraction of the sliding spinal rod 20 into the small diameter end 34 of the stepped passage 32. The locking of the sliding spinal rod 20 may prevent the rod system 10 from inadvertently lengthening during insertion.

Figure 18:
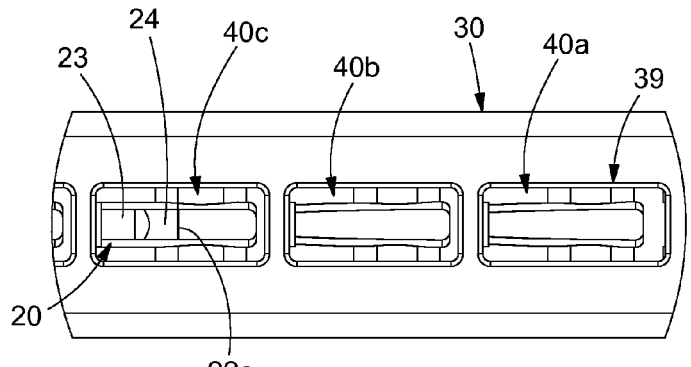
FIG. 18 is an enlargement of the detail area 18 shown in FIG. 15.

The first portion 21 of the sliding spinal rod 20 and the second section 52 of the fixed spinal rod 50 are inserted into a pedicle screw saddle, hook saddle, or the like of respective pedicle screws (not shown) secured in vertebrae of a patient. The length of rod system 10 is adjusted to a desired length by extending the sliding spinal rod 20 from the housing 30 as shown in FIGS. 15-18. The position of the sliding spinal rod 20 may be viewed through the cutouts 39 of the housing 30 to determine the length of the sliding spinal rod 20 disposed within housing 30 as shown in FIG. 18. In embodiments where the sliding spinal rod 20 is locked by a set screw 38, the set screw 38 is loosened and/or removed to permit the sliding spinal rod 20 to extend from the housing 30. The first portion 21 and the second section 52 are then secured to the respective pedicle screws when the rod system 10 is set to the desired length. The sliding spinal rod 20 may be locked by tightening the set screw 38 adjacent the small diameter end 34 or be left free. When the sliding spinal rod 20 is left free or unlocked, the rod system 10 permits the sliding spinal rod 20 to extend from the housing 30 in response to the natural growth of the patient while maintaining the spinal construct in a desired position relative to the anatomy of the patient. Permitting the spinal rod 20 to extend from the housing 30 in this manner may avoid the need for subsequent surgeries to adjust the rod system 10 as the height of the patient increases. Alternatively, if the sliding spinal rod 20 is locked in place by tightening set screw 38 adjacent the small diameter end 34, the surgeon during subsequent surgery may loosen the set screw and adjust the position of the sliding spinal rod relative to the housing to accommodate for patient healing or growth, and optionally may re-lock the sliding spinal rod to the housing by re-tightening the set screw. As described above, as the sliding spinal rod is adjusted to protrude further out of the housing, the ribs of the spacers inhibit the sliding spinal rod from sliding back into the housing which would result in shortening of the screw-rod construct.

In aspects of the present disclosure, the housing 30 described above may be constructed of a variety of biocompatible materials, e.g., stainless steel, cobalt chrome, PEEK, titanium, titanium alloys, etc.

In aspects of the present disclosure, the spacers 40 described above may be constructed of a variety of biocompatible materials, e.g., polymers, nitinol, stainless steel, titanium, etc.

In aspects of the present disclosure, the sliding and fixed spinal rods 20, 50 described above may be made in various diameters and various shapes and may be constructed of a variety of biocompatible materials, e.g., stainless steel, cobalt chrome, PEEK, titanium, titanium alloys, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A growing spinal rod system comprising:
   a housing defining a longitudinal axis and a stepped passage, the stepped passage disposed about the longitudinal axis and having a first end and a second end, a diameter of the first end being less than a diameter of the second end;
   a first spacer disposed within the stepped passage of the housing about the longitudinal axis, the first spacer including a ring defining a through hole coaxial with the longitudinal axis and a plurality of ribs extending from the ring towards the first end of the stepped passage, the plurality of ribs biased radially inwards, the first spacer includes a plurality of mating protrusions extending from the ring towards the second end of the stepped passage, the plurality of ribs of the first spacer define mating slots between adjacent ribs, each mating slot sized and configured to receive a respective mating protrusion of a second spacer;
   a first spinal rod slidably inserted through the through hole of the first spacer and extending from the housing through the first end of the stepped passage, the first spinal rod moving the plurality of ribs outwards when the first spinal rod is inserted through the through hole of the first spacer, the plurality of ribs permitting the first spinal rod to extend from the housing through the first end of the stepped passage and inhibiting the first spinal rod from retracting into the housing through the first end of the stepped passage; and
   a second spinal rod including an end slidably received through the second end of the stepped passage.

2. The growing spinal rod system of claim 1, wherein the first end of the stepped passage includes a flat first keyed surface and the first spinal rod includes a longitudinal groove, the groove mating with the first keyed surface of the first end to rotatably fix the first spinal rod relative to the housing.

3. The growing spinal rod system of claim 2, wherein the first spinal rod includes a first portion having a first diameter and a second portion having a second diameter larger than the first diameter of the first portion, the groove being formed in the second portion.

4. The growing spinal rod system of claim 3, wherein the housing defines at least one blind hole orthogonal to the longitudinal axis, the at least one blind hole adjacent the first end of the stepped passage, the at least one blind hole penetrating the stepped passage.

5. The growing spinal rod system of claim 4, wherein the housing includes a set screw insertable through the at least one blind hole adjacent the first end to limit the travel of the first spinal rod relative to the housing.

6. The growing spinal rod system of claim 3, wherein the groove is defined substantially along a length of the second portion and the second portion includes a lip adjacent an end of the second portion extending above the groove, the lip configured to stop the end of the second portion from extending through the first end of the stepped passage.

7. The growing spinal rod system of claim 1, wherein the end of the second spinal rod engages the ring of the at least one spacer.

8. The growing spinal rod system of claim 7, wherein the housing defines at least one blind hole orthogonal to the longitudinal axis, the at least one blind hole adjacent the second end of the stepped passage, the at least one blind hole penetrating the stepped passage.

9. The growing spinal rod system of claim 8, wherein the housing includes a set screw insertable through the at least one blind hole adjacent the second end to longitudinally fix the second spinal rod relative to the housing.

10. The growing spinal rod system of claim 7, wherein the second end of the stepped passage includes a flat second keyed surface and the end of the second spinal rod includes a flat top surface that mates with the second keyed surface of the second end to rotatably fix the second spinal rod relative to the housing.

11. The growing spinal rod system of claim 1, wherein the first spacer includes a plurality of mating protrusions extending from the ring towards the second end of the stepped passage.

12. The growing spinal rod system of claim 1, wherein each of the mating protrusions of the first spacer are received by a respective mating slot of a second spacer.

13. The growing spinal rod system of claim 1, wherein the end of the second spinal rod defines mating recesses, each mating recess receiving a respective mating protrusion of the first spacer, the end of the second spinal rod engaging the ring of the first spacer when the mating protrusions are received within the mating recesses.

14. The growing spinal rod system of claim 1, wherein the housing includes a cutout configured to permit visualization of the stepped passage.

* * * * *